(12) United States Patent
Smith et al.

(10) Patent No.: US 12,594,428 B2
(45) Date of Patent: Apr. 7, 2026

(54) HAPTICS-BASED RECHARGE ALIGNMENT FEEDBACK FOR IMPLANTABLE STIMULATOR

(71) Applicant: Medtronic, Inc., Minneapolis, MN (US)

(72) Inventors: Brian A. Smith, Apple Valley, MN (US); Jeffery M. Kramer, St. Louis Park, MN (US); Andrew L. Schmeling, Holmen, WI (US); Andrew T. Fried, St. Paul, MN (US); Todd D. Zenisek, Georgetown, TX (US)

(73) Assignee: Medtronic, Inc., Minneapolis, MN (US)

( * ) Notice: Subject to any disclaimer, the term of this patent is extended or adjusted under 35 U.S.C. 154(b) by 379 days.

(21) Appl. No.: 18/311,852

(22) Filed: May 3, 2023

(65) Prior Publication Data

US 2023/0355983 A1     Nov. 9, 2023

Related U.S. Application Data

(60) Provisional application No. 63/364,286, filed on May 6, 2022.

(51) Int. Cl.
| | |
|---|---|
| *A61N 1/36* | (2006.01) |
| *A61N 1/02* | (2006.01) |
| *A61N 1/372* | (2006.01) |

(52) U.S. Cl.
CPC ......... *A61N 1/36139* (2013.01); *A61N 1/025* (2013.01); *A61N 1/36171* (2013.01); *A61N 1/372* (2013.01)

(58) Field of Classification Search
CPC ............................ A61N 1/3787; A61N 1/0551
See application file for complete search history.

(56) References Cited

U.S. PATENT DOCUMENTS

| | | | |
|---|---|---|---|
| 5,897,576 A | 4/1999 | Olson et al. | |
| 6,431,748 B1 | 8/2002 | Baratta | |

(Continued)

FOREIGN PATENT DOCUMENTS

| | | |
|---|---|---|
| CN | 111459212 A | 7/2020 |
| WO | 2013158238 A2 | 10/2013 |

(Continued)

OTHER PUBLICATIONS

"Living with Medtronic Bladder or Bowel Control Therapy Delivered by the InterStim™ Micro System," Medtronic Therapy Guide, 2020 (Applicant points out, in accordance with MPEP 609.04(a), that the year of publication, 2020, is sufficiently earlier than the effective U.S. filing date, so that the particular month of publication is not in issue.), 17 pp.

(Continued)

*Primary Examiner* — Carl H Layno
*Assistant Examiner* — Bryan Mcallister Lee
(74) *Attorney, Agent, or Firm* — Shumaker & Sieffert, P.A.

(57) ABSTRACT

Techniques to provide haptic feedback to a patient to help the patient align a medical device to a location on their anatomy. In some examples, the patient may align a recharging device to a medical device that is implanted at the location on their anatomy. In some examples, the electrical stimulation can be delivered in such a way that the patient may or may not be able to feel the electrical stimulation, e.g., experience a paresthesia sensation. The system of this disclosure may intentionally adjust the stimulation intensity to provide patient feedback for alignment, such as alignment of the recharging device with the implanted device. Alignment of the recharging device with the implanted device may improve energy transfer, which may, for example, recharge the implanted device more efficiently.

20 Claims, 5 Drawing Sheets

(56) References Cited

U.S. PATENT DOCUMENTS

| | | | |
|---|---|---|---|
| 6,681,135 | B1 | 1/2004 | Davis et al. |
| 7,167,756 | B1 | 1/2007 | Torgerson et al. |
| 7,952,322 | B2 | 5/2011 | Partovi et al. |
| 8,244,367 | B2 | 8/2012 | Wahlstrand et al. |
| 8,335,569 | B2 | 12/2012 | Aghassian |
| 8,457,744 | B2 | 6/2013 | Janzig et al. |
| 8,496,646 | B2 | 7/2013 | Kamen |
| 8,554,322 | B2 | 10/2013 | Olson et al. |
| 8,784,364 | B2 | 7/2014 | Kamen |
| 8,901,878 | B2 | 12/2014 | Prutchi et al. |
| 8,907,531 | B2 | 12/2014 | Hall et al. |
| 9,176,163 | B2 | 11/2015 | Heath |
| 9,209,634 | B2 | 12/2015 | Cottrill et al. |
| 9,225,190 | B2 | 12/2015 | Labbe et al. |
| 9,227,076 | B2 | 1/2016 | Sharma et al. |
| 9,270,134 | B2 | 2/2016 | Gaddam et al. |
| 9,461,476 | B2 | 10/2016 | Kamata |
| 9,653,935 | B2 | 5/2017 | Cong et al. |
| 9,851,372 | B2 | 12/2017 | Heath et al. |
| 9,929,584 | B2 | 3/2018 | Aghassian et al. |
| 9,958,351 | B2 | 5/2018 | Kuhn et al. |
| 10,105,103 | B2 | 10/2018 | Goldshtein et al. |
| 10,192,830 | B2 | 1/2019 | Rogers et al. |
| 10,258,804 | B2 | 4/2019 | Scott et al. |
| 10,554,069 | B2 | 2/2020 | Paralikar et al. |
| 10,672,530 | B2 | 6/2020 | Ronay |
| 10,686,337 | B2 | 6/2020 | Roy et al. |
| 10,971,943 | B2 | 4/2021 | Paralikar et al. |
| 11,394,226 | B2 | 7/2022 | Cong et al. |
| 11,705,763 | B2 | 7/2023 | Fried et al. |
| 11,752,355 | B2 | 9/2023 | Fried et al. |
| 2003/0050557 | A1 | 3/2003 | Susil et al. |
| 2005/0283144 | A1 | 12/2005 | Shiono et al. |
| 2006/0247738 | A1 | 11/2006 | Schmeling et al. |
| 2007/0129767 | A1 | 6/2007 | Wahlstrand |
| 2007/0156179 | A1 | 7/2007 | S.E. |
| 2007/0167997 | A1 | 7/2007 | Forsberg et al. |
| 2008/0272742 | A1 | 11/2008 | Hart et al. |
| 2009/0112291 | A1 | 4/2009 | Wahlstrand et al. |
| 2009/0276014 | A1 | 11/2009 | Morgan et al. |
| 2010/0217360 | A1 | 8/2010 | Henriksson |
| 2010/0234921 | A1 | 9/2010 | Torgerson et al. |
| 2010/0256710 | A1 | 10/2010 | Dinsmoor et al. |
| 2011/0077720 | A1 | 3/2011 | Torgerson et al. |
| 2012/0053657 | A1 | 3/2012 | Parker et al. |
| 2013/0193914 | A1 | 8/2013 | Gaddam et al. |
| 2013/0278226 | A1 | 10/2013 | Cong et al. |
| 2014/0048174 | A1 | 2/2014 | Lanigan |
| 2014/0379047 | A1 | 12/2014 | Meskens |
| 2015/0047947 | A1 | 2/2015 | Tait |
| 2015/0157869 | A1 | 6/2015 | Torgerson et al. |
| 2016/0187272 | A1 | 6/2016 | Ishii |
| 2016/0322156 | A1 | 11/2016 | Yeh et al. |
| 2017/0054213 | A1 | 2/2017 | Singh et al. |
| 2017/0083064 | A1 | 3/2017 | Mittal et al. |
| 2018/0159361 | A1 | 6/2018 | Cong et al. |
| 2018/0280708 | A1 | 10/2018 | Escalona et al. |
| 2018/0301923 | A1 | 10/2018 | White, II et al. |
| 2019/0098129 | A1 | 3/2019 | Frieding et al. |
| 2019/0190296 | A1 | 6/2019 | Paralikar et al. |
| 2019/0229770 | A1 | 7/2019 | Khaleghi et al. |
| 2019/0290819 | A1 | 9/2019 | Hansen |
| 2019/0358395 | A1 | 11/2019 | Olson et al. |
| 2020/0015678 | A1 | 1/2020 | Li et al. |
| 2020/0136417 | A1 | 4/2020 | Paralikar et al. |
| 2020/0306528 | A1* | 10/2020 | Linden ............... A61N 1/37223 |
| 2021/0119469 | A1 | 4/2021 | Cong et al. |
| 2021/0121708 | A1 | 4/2021 | Fried et al. |
| 2021/0226471 | A1 | 7/2021 | Paralikar et al. |
| 2022/0134116 | A1 | 5/2022 | Fried et al. |
| 2022/0149671 | A1* | 5/2022 | Sama ..................... H02J 50/80 |
| 2023/0045477 | A1 | 2/2023 | Fried |

FOREIGN PATENT DOCUMENTS

| | | |
|---|---|---|
| WO | 2016172530 A1 | 10/2016 |
| WO | 2017053067 A1 | 3/2017 |

OTHER PUBLICATIONS

Colombo, "An Integrated Mechatronic Unit to Control Heating Power of an Electronic Diesel Fuel Heater," Proceedings of the IEEE International Symposium on Industrial Electronics, Dubrovnik, Croatia, ISIE 2005, doi:10.1109/ISIE.2005.1528926, Jun. 20-23, 2005, 6 pp.

U.S. Appl. No. 18/330,152, filed Jun. 6, 2023, by Fried et al.

* cited by examiner

170

105

150

152

SERVER
112

FRONT

105

120

132A     132B

130A

130B 116  172

150

REAR

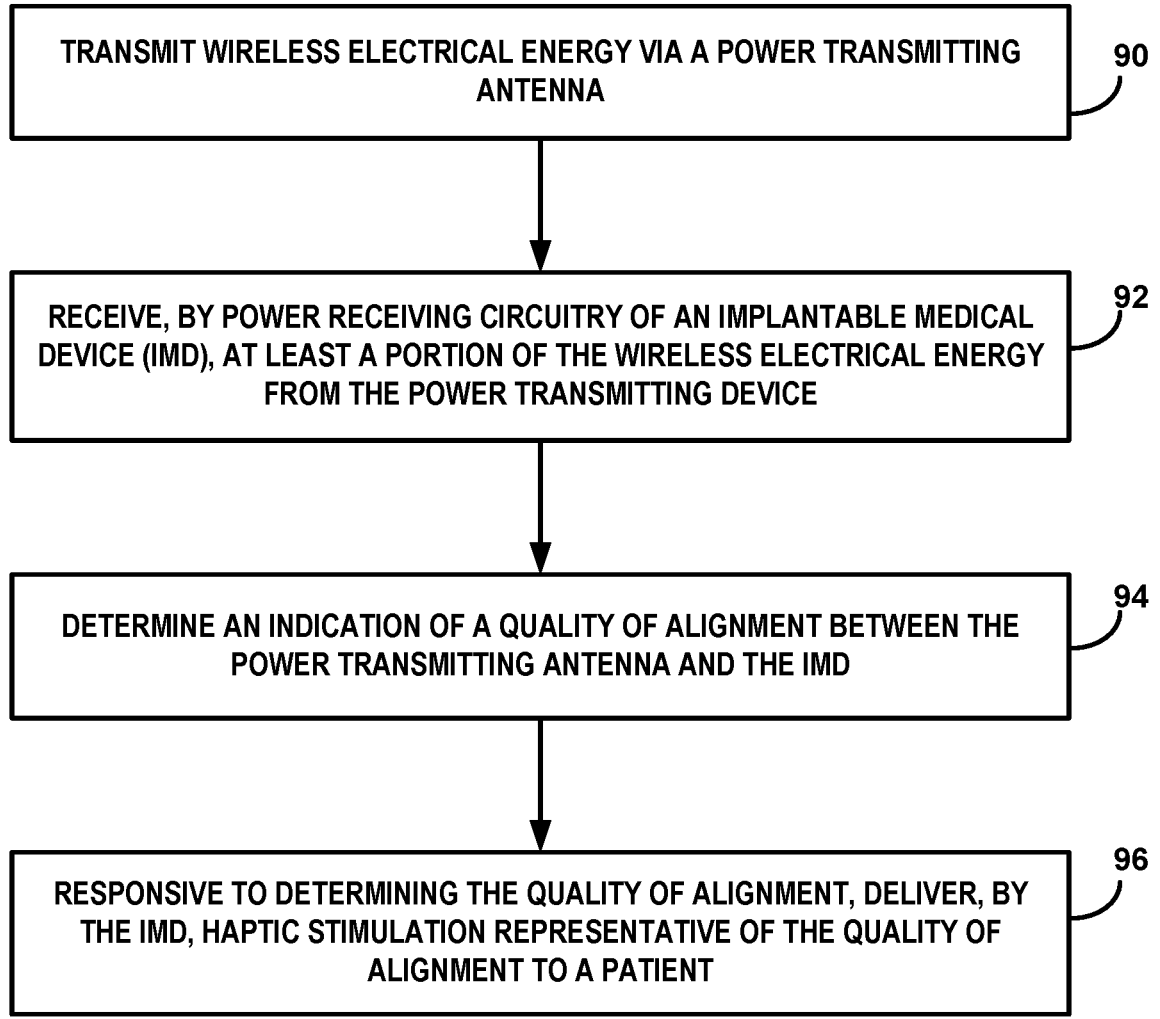

TRANSMIT WIRELESS ELECTRICAL ENERGY VIA A POWER TRANSMITTING ANTENNA — 90

RECEIVE, BY POWER RECEIVING CIRCUITRY OF AN IMPLANTABLE MEDICAL DEVICE (IMD), AT LEAST A PORTION OF THE WIRELESS ELECTRICAL ENERGY FROM THE POWER TRANSMITTING DEVICE — 92

DETERMINE AN INDICATION OF A QUALITY OF ALIGNMENT BETWEEN THE POWER TRANSMITTING ANTENNA AND THE IMD — 94

RESPONSIVE TO DETERMINING THE QUALITY OF ALIGNMENT, DELIVER, BY THE IMD, HAPTIC STIMULATION REPRESENTATIVE OF THE QUALITY OF ALIGNMENT TO A PATIENT — 96

FIG. 4

HAPTICS-BASED RECHARGE ALIGNMENT FEEDBACK FOR IMPLANTABLE STIMULATOR

This Application claims the benefit of U.S. Provisional Patent Application 63/364,286, filed 6 May 2022, the entire content of which is incorporated herein by reference.

TECHNICAL FIELD

The disclosure relates to implantable medical devices, and more particularly to transcutaneous recharging of implantable medical devices.

BACKGROUND

Medical devices may be external or implanted and may be used to monitor patient signals such as cardiac activity, biological impedance and to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis and other conditions. In some examples, medical devices may include a rechargeable electrical power source, or may be powered directly by transmitting energy through tissue.

SUMMARY

In general, the disclosure describes devices, systems, and techniques to provide haptic feedback to a patient to help the patient align a medical device to a location on their anatomy. In some examples, the patient may align a recharging device to a medical device that is implanted at the location on their anatomy. Alignment of the recharging device with the implanted device may improve energy transfer, which may, for example, recharge the implanted device more efficiently (e.g., less time and/or less heating during recharge).

An implantable medical device may deliver electrical stimulation therapy to the patient, and periodically need to receive recharge energy to replenish the battery, or a similar energy storage unit. In some examples, the electrical stimulation can be delivered in such a way that the patient may or may not be able to feel the electrical stimulation, e.g., experience a paresthesia sensation. The implantable medical device may be programmed to deliver stimulation therapy with a stimulation intensity set at an intensity to relieve the patient's symptoms, e.g., pain, tremors, and so on, but also relative to the patient's perception threshold or sensory threshold. The system of this disclosure may intentionally adjust the stimulation intensity to provide patient feedback for alignment, such as alignment of the recharging device with the implanted device.

In one example, this disclosure describes an implantable medical device comprising a memory; power receiving circuitry, configured to receive wireless electrical energy; stimulation generation circuitry configured to deliver electrical stimulation therapy to the patient via a plurality of electrodes; and processing circuitry operably coupled to the memory, the processing circuitry configured to: control the stimulation generation circuitry to deliver the electrical stimulation therapy to a patient; receive an indication of a quality of alignment with a power transmitting device; responsive to the indication of the quality of alignment, cause the stimulation generation circuitry to deliver haptic stimulation representative of the quality of alignment.

In another example, this disclosure describes a method comprising transmitting, by a power transmitting device, wireless electrical energy via a power transmitting antenna; receiving, by power receiving circuitry of an implantable medical device (IMD), at least a portion of the wireless electrical energy from the power transmitting device; determining an indication of a quality of alignment between the power transmitting antenna and the IMD; responsive to determining the quality of alignment, delivering, by the IMD, haptic stimulation representative of the quality of alignment to a patient.

In another example, this disclosure describes a system comprising a power transmitting device configured to wirelessly transfer electrical energy, the power transmitting device including power transmission circuitry configured to wirelessly output the electrical energy via the power transmitting antenna; and first processing circuitry, the processing circuitry configured to control the power transmission circuitry; and an implantable medical device (IMD) comprising: power receiving circuitry configured to receive at least a portion of wireless electrical energy from the power transmitting device; stimulation generation circuitry configured to deliver electrical stimulation therapy to a patient via a plurality of electrodes; and second processing circuitry, the second processing circuitry configured to: control the stimulation generation circuitry; receive an indication of a quality of alignment with the power transmitting antenna; and responsive to receiving the indication of the quality of alignment, cause the stimulation generation circuitry to deliver haptic stimulation representative of the quality of alignment.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 4 is a flowchart illustrating an example operation of the medical system of this disclosure.

DETAILED DESCRIPTION

Figure 1A:
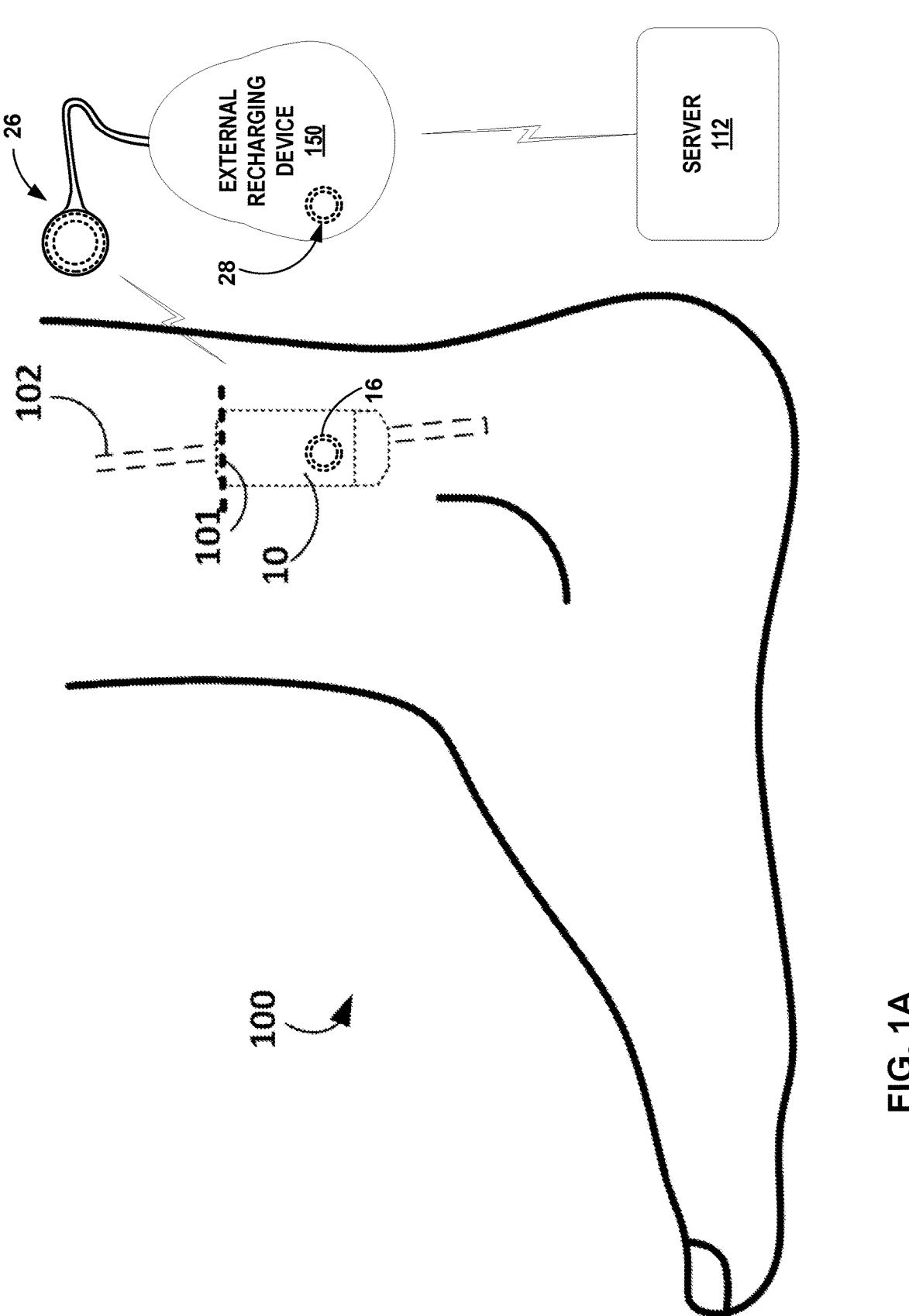
FIG. 1A is a conceptual diagram illustrating a medical system of this disclosure that includes an implantable medical device located near a hip of a patient.

Devices, system, and techniques configured to provide haptic feedback to a patient to help the patient align a medical device to a location on their anatomy are described herein. In some examples, the patient may align a recharging device to a medical device that is implanted at the location on their anatomy. Alignment of the recharging device with the implanted device may improve energy transfer, which may, for example, recharge the implanted device more efficiently and take less time. Less recharging time may be more convenient for the patient. In other examples, the patient may align a medical device to a specified location on their anatomy to provide external sensing, monitoring, therapy delivery, including electrical stimulation therapy, drug delivery therapy and so on.

In the example of a rechargeable device, recharger head alignment with an implantable device is desirable for optimal recharging. In some examples, the better the recharger head, containing a recharge coil, and the implantable receiver coil are aligned, the better the energy transfer may be. In some examples, a medical system may include a user interface to provide users feedback on recharge coupling to help the patient better align the recharger. The user interface may include a display screen that may provide a graphical indication of alignment. In some examples, the implant location may be near the posterior side of the patient, such as near the hip or spinal cord, which may make it awkward for some patients to align their recharger head with their implantable device. In some examples, a patient may establish good recharger alignment, but then during the course of recharging (which may take an hour or more), the recharger may become less well-aligned to the implant.

In the example of a medical device that delivers electrical stimulation therapy, the electrical stimulation can be delivered in such a way that the patient may or may not be able to feel the electrical stimulation, e.g., experience a paresthesia sensation. The implantable medical device may be programmed to deliver stimulation therapy with a stimulation intensity set at an intensity to relieve the patient's symptoms, e.g., pain, tremors, and so on, but also relative to the patient's sensation perception threshold. For example, some patients may prefer to feel some level of stimulation, e.g., to know the therapy is being delivered, while in other examples, patients may find the perception of stimulation annoying.

The system of this disclosure may intentionally adjust the stimulation intensity to a level that is perceptible in some way, different from therapy, to provide patient feedback for alignment, such as alignment of the recharging device with the implanted device. A patient may experience qualitatively different sensations when receiving various stimulation pulses. For example, stimulation with a low frequency such as four Hertz (4 Hz) may be experienced as a thumping or tapping sensation. A frequency of 50 Hz may be experienced as a buzzing or tingling sensation. Adjusting the stimulation intensity above and below the sensation threshold of the patient may cause the patient to alternately become aware of the sensation and then lose the sensation, which may provide haptics feedback to adjust the alignment.

After recharge has been initiated, the implantable device may adjust stimulation in such a way to indicate improving recharger alignment. For example, when the recharger is in weak alignment, stimulation may alternate between 4 Hz and 50 Hz. As alignment improved, the system may adjust various aspects of the delivered stimulation to indicate the changes in alignment. In some examples, the system may adjust frequency alternation interval, the stimulation intensity, change to a higher or lower frequency, and so on. In some examples, the haptics sensation may be selectable by the patient or a caregiver, e.g., by selecting from one or more options during post-implant care by using an external programming device.

One benefit of the approach of this disclosure is that the haptics sensation may enable a feedback mechanism that does not require visual attention to a graphical display on a screen or to an audible tone. Also, while patients may be able to achieve initial alignment, should the recharger become misaligned during the recharging process, the haptics feedback techniques of this disclosure may draw the patient's attention back to the lost alignment and prompt the patient to improve the alignment of the recharger with the implantable medical device.

FIG. 1A is a conceptual diagram illustrating an example medical system 100 of this disclosure that includes an implantable medical device located near an ankle of a patient. The example of system 100 in FIG. 1A includes an implantable medical device 10, external computing device 150, and one or more servers 112. External computing device 150 may also be referred to as external recharging device 150 or recharger 150.

External computing device 150 includes one or more antenna, such as antenna 26 and antenna 28. External computing device 150 may be used to program or adjust settings of device 10 and may also recharge an electrical energy storage device, such as a battery, of device 10. External computing device 150 may also communicate with one or more servers 112. In other examples, a computing device separate from external computing device 150 (not shown in FIG. 1) may communicate with device 10 to adjust therapy and/or sensing parameters, download recorded data, and so on.

The example of FIG. 1A is a side view of a patient's leg showing a leadless neurostimulation device 10 near the ankle adjacent to the tibial nerve 102. Device 10 can be implanted through the patient's skin and cutaneous fat layer via a small incision 101 (e.g., about one to three cm) above the tibial nerve on a medial aspect of the patient's ankle. While incision 101 is shown approximately horizontal to the length of the tibial nerve, other incisions or implantation techniques could be used according to physician preference. The example of FIG. 1A describes a neurostimulation implantable medical device for tibial nerve stimulation. In other examples, the techniques of this disclosure may apply to other rechargeable devices, such as implantable neurostimulation system for use in spinal cord stimulation therapy, deep brain stimulation, as well as to other types of medical devices without limitation. In this disclosure, device 10 may referred to as an implantable medical device (IMD) 10 or, in the example of a neurostimulation medical device, may be referred to as implantable neuro stimulator (INS) 10.

Device 10 may be positioned adjacent to the region defined by flexor digitorum longus and soleus in which tibial nerve 102 is contained and implanted adjacent and proximal to a fascia layer. One or more electrodes of device 10 may face toward tibial nerve 102. Other electrodes, e.g., electrodes 15 may be located in other positions on device 10. Though not shown in FIG. 1A, device 10 may also connect to one or more leads comprising one or more electrodes (not shown in FIG. 1A).

Device 10 may be constructed of any polymer, metal, or composite material sufficient to house the components of device 10. In this example, device 10 may be constructed with a biocompatible housing, such as titanium or stainless steel, or a polymeric material such as silicone or polyurethane, and surgically implanted at a site in patient near the tibial nerve, in some examples, while in other examples, implanted near the pelvis, abdomen, or buttocks. The housing of device 10 may be configured to provide a hermetic seal for components, such as a rechargeable power source. In addition, the housing of device 10 may be selected of a material that facilitates receiving energy to charge the rechargeable power source.

Optional testing of neurostimulation device 10 may be performed to determine if device 10 has been properly positioned in proximity to tibial nerve 102 to elicit a desired response from an applied electrical stimulation. In an example, device 10 is controlled by an external programmer to deliver test stimulation, and one or more indicative responses are monitored, such as toe flexion from simulation of the tibial motor neurons controlling the flexor hallucis brevis or flexor digitorum brevis, or a tingling sensation in the heel or sole of the foot excluding the medial arch. If such testing does not elicit appropriate motor or sensory responses, the practitioner may reposition device 10 and retest.

Once a practitioner has determined device 10 is properly positioned to provide an appropriate patient response to delivered stimulation therapy, the housing of device can be secured in place if needed. Such anchoring means may be optional as the natural shape of the region in which device 10 is implanted, and the shape of device 10 itself may have good compatibility with the surrounding tissue thus preventing device 10 from shifting or rolling after implantation. In some examples, leadless neurostimulation device 10 may further include one or more suture points to help secure device 10 to fascia or other parts of the patient. In some examples, a suture anchor may be included, such as at the distal end of the housing of device 10.

An advantage of the devices and methods described herein can be improved patient safety and satisfaction after implant. In contrast to other approaches, leadless neurostimulation device 10 may not require the patient's fascia layer near the implant site to be disturbed which may reduce risks affiliated with alternative procedures. Further, device 10 is a unitary structure and may be hermetically sealed.

During normal operation after implantation, an electrical stimulation signal may be transmitted between one or more electrodes through the fascia layer. The electrical signal may be used to stimulate tibial nerve 102 which may be useful in the treatment of overactive bladder (OAB) symptoms of urinary urgency, urinary frequency and/or urge incontinence, or fecal incontinence.

One type of therapy for treating bladder dysfunction includes delivery of electrical stimulation to a target tissue site within a patient to cause a therapeutic effect during delivery of the electrical stimulation. For example, delivery of electrical stimulation from device 10 to a target therapy site, e.g., a tissue site that delivers stimulation to modulate activity of a tibial nerve, spinal nerve (e.g., a sacral nerve), a pudendal nerve, dorsal genital nerve, an inferior rectal nerve, a perineal nerve, or branches of any of the aforementioned nerves, may provide a therapeutic effect for bladder dysfunction, such as a desired reduction in frequency of bladder contractions. In some cases, electrical stimulation of the tibial nerve may modulate afferent nerve activities to restore urinary function.

In the example of a rechargeable power source, the rechargeable power source of device 10 may include one or more capacitors, batteries, or other components (e.g., chemical, or electrical energy storage devices). Example batteries may include lithium-based batteries, nickel metal-hydride batteries, or other materials. The rechargeable power source may be replenished, refilled, or otherwise capable of increasing the amount of energy stored after energy has been depleted. The energy received from secondary coil 16 may be conditioned and/or transformed by a charging circuit. The charging circuit may then send an electrical signal used to charge the rechargeable power source when the power source is fully depleted or only partially depleted.

External computing device 150 may be used to recharge the rechargeable power source within device 10 implanted in the patient. External computing device 150 may be a handheld device, a portable device, or a stationary charging system. External computing device 150 may include components necessary to charge device 10 through tissue of the patient. External computing device 150 may include an internal energy transfer coil 28 and external energy transfer coil 26, also referred to as primary coil 26 or primary coil 28. In other examples, external computing device may only include internal primary coil 28 and omit the use of external primary coil 26.

External computing device 150 may include a housing to enclose operational components such as a processor, memory, user interface, telemetry circuitry, power source, and charging circuit configured to transmit energy to secondary coil 16 via energy transfer coil 26 and/or 28. Although a user may control the recharging process with a user interface of external computing device 150, external computing device 150 may alternatively be controlled by another device, e.g., an external programmer, a computing device of servers 112, where such servers may include a tablet computer, laptop or other similar computing device. External computing device 150, and any computing device of servers 112 may include a touch-screen user interface. In other examples, external computing device 150 may be integrated with an external programmer, such as a patient programmer carried by the patient.

External computing device 150 and device 10 may utilize any wireless power transfer techniques that are capable of recharging the power source of device 10 when device 10 is implanted within the patient. In some examples, system 100 may utilize inductive coupling between primary coils (e.g., energy transfer coil 28) and secondary coils (e.g., secondary coil 16) of external computing device 150 and device 10. In inductive coupling, energy transfer coil 28 is placed near implanted device 10 such that energy transfer coil 28 is aligned with secondary coil 16 of device 10. External computing device 150 may then generate an electrical current in energy transfer coil 28 based on a selected power level for charging the rechargeable power source of device 10. When the primary and secondary coils are aligned, or partially aligned, the electrical current in the primary coil may magnetically induce an electrical current in secondary coil 16 within device 10. Since the secondary coil is associated with and electrically coupled to the rechargeable power source, the induced electrical current may be used to increase the voltage, or charge level, of the rechargeable power source. Although inductive coupling is generally described herein, any type of wireless energy transfer may be used to transfer energy between external computing device 150 and device 10.

The degree (or quality) of alignment of a primary coil (either coil 26 or 28) with secondary coil 16 may affect the efficiency of the energy transfer between external computing device 150 and device 10. Energy transfer efficiency may be calculated in several ways, such a ratio between the amount of power produced by the primary coil and the amount of power received by the secondary coil. In some examples, an efficient energy transfer alignment may be when the primary coil, e.g., coil 28 is concentric with secondary coil 16. In other examples, an energy efficient transfer alignment may be when the primary coil center is offset from the center of the secondary coil. In any event, the components of system 100 may be configured to provide haptic feedback to a patient to help spatially align the primary and secondary coils that enable an efficient transfer alignment. In less efficient alignments, the energy produced by the primary coil 28 results in less current induced in secondary coil 16. For example, processing circuitry within device 10 (not shown in FIG. 1) may receive an indication of a quality of alignment with power transmitting device, e.g., a primary coil of external computing device 150. As noted above, the indication of the quality of alignment may include any of several system metrics to determine the quality of alignment, such as power transfer efficiency, the magnitude of current induced in device 10, a measure of heating within device 10, or any other indication of energy transfer efficiency and/or alignment. Responsive to the indication of the quality of alignment, the processing circuitry of device 10 may cause the stimulation generation circuitry of device 10 (not shown in FIG. 1) to deliver haptic stimulation representative of the quality of alignment.

As noted above stimulation with a low frequency may be experienced as a tapping sensation, while a higher frequency, e.g., of 50 Hz, may be experienced as a buzzing or tingling sensation. In some examples, the delivered haptic stimulation may alternate between a low and higher frequency at a slow rate, such as alternating every one to three seconds. In some examples the alternation could be abrupt frequency changes, or could gradually sweep, e.g., increase and decrease in steps or continuously between the higher and lower frequencies. As alignment improved, the frequency alternation interval may decrease and one or both of the frequencies could increase. When the patient achieves excellent alignment, e.g., as measured by one or more system metrics, the frequencies could collapse to a single frequency to create a constant sensation. Alternatively, the stimulation amplitude at either frequency could pulsate to create a throbbing sensation that generally subsides to a constant sensation as excellence alignment is achieved. In other examples, the haptic stimulation may decrease below a perception threshold of the patient as the alignment quality increases. In some examples, intensity of the haptic stimulation may be inversely proportional to the quality of alignment. In other words, as the quality of alignment decreases, the intensity of the haptic stimulation increases above a perception threshold of the patient and vice versa. In other examples, as the quality of alignment decreases, the frequency alternation interval may increase or otherwise change to indicate the quality of alignment. In some examples, the haptic stimulation may be separate from stimulation therapy delivered to the patient (e.g., different waveforms and/or interleaved with the stimulation therapy). In other examples, the stimulation therapy may be altered in order to also provide haptic stimulation perceptible by the patient.

The processing circuitry of device 10 may control stimulation intensity by adjusting any of several stimulation parameters. Some examples may include increasing a pulse magnitude, e.g., increased current magnitude, may increase stimulation intensity, while decreasing pulse magnitude may decrease stimulation intensity. Similarly, changing other parameters, such as increasing a pulse width, or increasing the number of pulses in a burst may increase stimulation intensity. The processing circuitry may control the delivered haptic stimulation to above or below a perception threshold for a specific patient by adjusting any combination of electrical stimulation parameters. In some examples, the perception threshold may be determined based on patient feedback to identify stimulation parameters that would generate stimulation intensity at one or more levels above the perception threshold. In other examples, the perception threshold may be associated with a characteristic of sensed ECAP signals elicited by the stimulation, such that the system may compare the characteristics of sensed ECAP signals to a perception threshold characteristic and increase or decrease stimulation intensity in order to achieve a target level of haptic stimulation.

Energy transfer coil 26 and 28 may include a wound wire (e.g., a coil) (not shown in FIG. 1A). The coil may be constructed of a wire wound in an in-plane spiral (e.g., a disk-shaped coil). In some examples, this single or even multi-layers spiral of wire may be considered a flexible coil capable of deforming to conform with a non-planar skin surface. The coil may include wires that electrically couple the flexible coil to a power source and a charging module configured to generate an electrical current within the coil. Energy transfer coil 28 may be external of the housing of external computing device 150 such that energy transfer coil 28 can be placed on the skin of the patient proximal to device 10. In some examples, energy transfer coil 28 may be disposed on the outside of the housing or even within housing.

Either primary coil 26 and/or 28 of system 100 may include a heat sink device (not shown in FIG. 1A). In the example of system 100, external computing device 150 is the power transmitting unit and device 10 is the power receiving unit. device 10 may be in a flipped or non-flipped position.

As noted above, in this disclosure external computing device 150 may also be referred to as recharger 150. External computing device 150 may include a user interface to receive control inputs from a user, such as the patient, medical professional, or other caregiver. The user interface of external computing device 150 may also provide information to a user, including the quality of alignment, whether device 10 is ON and delivering therapy, whether external computing device 150 is wirelessly communicating with device 10 and so on.

The haptic stimulation techniques of this disclosure may provide additional information to the patient, as noted above, along with the information from the user interface of external computing device 150. The haptic stimulation techniques of this disclosure may be valuable when device 10 is implanted location on the hip or other location where it may be difficult to see a user interface of system 100 when aligning the primary and secondary coils, e.g., coils 28 and 16, as described above.

In other examples, the indication of the quality of alignment may be based on a determination that the power receiving device, e.g., device 10, is receiving power relative to a power threshold. The processing circuitry of device 10, responsive to determining that the device 10 is receiving wireless power above a first threshold and receiving wireless power below a second threshold, cause the electrical stimulation circuitry to deliver the haptic stimulation at a first frequency, e.g., a low frequency to cause a tapping sensation, or a higher frequency to cause a buzzing sensation. In some examples, responsive to determining that the power receiving device is receiving wireless power above the first threshold and above the second threshold, the processing circuitry may cause the electrical stimulation circuitry to deliver the haptic stimulation at a second frequency. In other words, the processing circuitry may change the frequency, or other parameters of the haptic stimulation, based on one or more predetermined thresholds of received power as measure of the quality of alignment. Some example thresholds of received power may include measured magnitude of current received by the energy storage device of device 10, such as a first threshold at ten milliamps, a second threshold at 100 milliamps, and so on. The processing circuitry of system 100 may use other thresholds on any of the variety of available system metrics.

In some examples, external computing device 150 may receive wireless communication from device 10 that include the amount of power delivered to the electrical energy storage device of device 10, which may be referred to as closed loop charging. In other words, system 100 may measure efficiency, such as IMD efficiency, to determine whether the relative position of primary coil 26 and secondary coil 16 may be in a less desirable relative position.

A variety of system metrics are available to external computing device 150 from computations of power and heat and from metrics communicated to the recharger from IMD 14. Processing circuitry of system 100, e.g., processing circuitry of external computing device 150, processing circuitry of servers 112, and/or processing circuitry of device 10, may calculate any of the values described herein. These metrics may include but are not limited to: battery current (Iins_batt), Power Transfer Efficiency (Pins_batt/Ptank), IMD Efficiency (Pins_batt/Qins) or (Pins_batt/Pins). Analysis of system characterization data that the IMD efficiency, which may be measured by device 10 and communicated to external computing device 150, may be an example indicator of when the recharger primary coil 26 is concentric with secondary coil 16. A concentric relative position of primary coil 26 and secondary coil 16 may be in positions with the lowest overall transient thermal response (increase in temp for the same heat). In some examples, the energy transfer in concentric positions (e.g., near 0, −20 in X and Y) may be higher and the battery of IMD 14 may charge faster.

Therefore, there may be an exponential relationship between the IMD efficiency, which may also be referred to as INS efficiency in this disclosure, and the overall thermal dose in units of CEM43 (i.e., an equivalent time at 43 degrees Celsius). The power transfer efficiency on the other hand may be more skewed towards the geometrical center of the device 10 (near 0, 0 in X and Y). In some examples both power transfer efficiency and IMD efficiency metrics may be lower when primary coil 26 is positioned over the header of device 10, which may lead to decreased efficiency and a less desirable thermal profile (e.g., an increase in temperature for the same heat). The header of device 10 may be non-metallic and contain connections for one or more leads connected to electrodes or other sensors. Furthermore, at such positions the time to charge may be longer so the overall thermal dose could be higher than quicker charging periods that result from more efficient coupling. In some examples, processing circuitry of external computing device 150 may determine the impedance of primary coil 28, or coil 26, to calculate an estimate for the amount of heating of the power receiving unit, e.g., device 10. The cost of suboptimal alignment is that recharging make take longer and may generate more heat, e.g., in device 10 and/or the surrounding tissue, than is strictly necessary. In this manner, the techniques of this disclosure may provide advantages over other subcutaneous wireless power transfer techniques by establishing, and maintaining, primary to secondary coil alignment.

In some examples, device 10 may receive communication that include quality of alignment data, e.g., one or more system metrics. Processing circuitry of device 10 may perform calculations to determine the type, intensity, and other parameters of the haptic stimulation based on the received quality of alignment data. In other examples, other processing circuitry of system 100 may receive quality of alignment data, calculate parameters for the haptic stimulation, and send commands to device 10 that include the calculated parameters and cause processing circuitry of device 10 to output the commanded haptic stimulation.

An evoked compound action potential (ECAP) is a signal recorded from a nerve trunk made up of numerous axons. It is the result of summation of many action potentials from the individual axons in the nerve trunk. An ECAP may be initiated on a nerve by an electrical stimulus applied to the nerve at some point at a distance from the recording site. The amplitude of the recorded compound action potential is a summation of the individual action potentials from the different axons. In other words, the ECAP may represent a synchronized response generated by a group of electrically activated nerve fibers. ECAPs sensing may further enables the processing circuitry of device 10 to be aware of whether the patient may be experience a sensation. In some examples, the programming instructions executed by processing circuitry of system 100 to apply the approach of this disclosures may be further enhanced by using ECAPs to govern the level of stimulation to ensure the stimulation is delivered at the appropriate level above perception threshold. For example, system 100 may sense ECAP signals elicited by delivered stimulation (e.g., haptic stimulation and/or stimulation therapy) and adjust the delivered stimulation in order to achieve target ECAP signals representative of the level of stimulation appropriate to indicate the alignment during recharge.

Figure 1B:
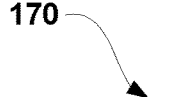
FIG. 1B is a conceptual diagram illustrating a medical system of this disclosure that includes an implantable medical device located near an ankle of a patient.

FIG. 1B is a conceptual diagram illustrating an example system 170 that includes an IMD 172 configured to deliver spinal cord stimulation (SCS) therapy and an external computing device 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices. In the example of FIG. 1B, system 170 includes IMD 172 with antenna 116, external computing device 150 and servers 112, which are, respectively examples of IMD 110 with antenna 16, external computing device 150 and servers 112 described above in relation to FIG. 1A and may have the same or similar functions and characteristics.

As shown in FIG. 1B, system 170 includes an IMD 172, leads 130A and 130B, and external computing device 150 shown in conjunction with a patient 105, who is ordinarily a human patient. In the example of FIG. 1B, IMD 172 is an implantable electrical stimulator that is configured to generate and deliver electrical stimulation therapy to patient 105 via one or more electrodes of electrodes 132A and 132B, respectively on leads 130A and/or 130B (collectively, "leads 130"), e.g., for relief of chronic pain or other symptoms. In other examples, IMD 172 may be coupled to a single lead carrying multiple electrodes or more than two leads each carrying multiple electrodes. IMD 172 may include an electrical connector configured to connect to the electrical leads, e.g., in the header of IMD 172. In other examples, IMD 172 may include electrodes in contact with patient tissue on the device and not connected through leads 130, similar to IMD 10 described above in relation to FIG. 1A.

IMD 172 may be a chronic electrical stimulator that remains implanted within patient 105 for weeks, months, or even years. In other examples, IMD 172 may be a temporary, or trial, stimulator used to screen or evaluate the efficacy of electrical stimulation for chronic therapy. In one example, IMD 172 is implanted within patient 105, while in another example, IMD 172 is an external device coupled to percutaneously implanted leads.

In some examples, the stimulation signals, or pulses, may be configured to elicit detectable ECAP signals that IMD 172 may use to determine the posture state occupied by patient 105 and/or determine how to adjust one or more parameters that define stimulation therapy. The processing circuitry of IMD 172 may cause the stimulation signals to also deliver haptic stimulation, e.g., stimulation above a perception threshold of patient 105, to provide patient feedback, such as feedback on the quality of alignment between the primary and secondary coils.

This disclosure will focus on a device used for spinal cord stimulation, as shown in the example of FIG. 1B to simplify the description. However, the techniques of this disclosure may also apply to other devices, including wearable devices, that may be located elsewhere on patient 105. Some examples may include devices located near the head for DBS, near the tibial region as in the example of FIG. 1A, near the heart for cardiac therapy and/or monitoring, and so on.

In other words, although in one example IMD 172 takes the form of an SCS device, in other examples, IMD 172 takes the form of any combination of deep brain stimulation (DBS) devices, implantable cardioverter defibrillators (ICDs), pacemakers, cardiac resynchronization therapy devices (CRT-Ds), left ventricular assist devices (LVADs), implantable sensors, orthopedic devices, or drug pumps, as examples. Moreover, techniques of this disclosure may be used to determine parameters that affect stimulation thresholds (e.g., perception thresholds and detection thresholds) associated any one of the aforementioned IMDs and then use a stimulation threshold to inform the intensity (e.g., stimulation levels) of therapy. For example, changing stimulation parameters such as the number of pulses in a burst, the number of bursts over a duration, the pulse width of a pulse in a burst, the ON-time, the OFF-time, a pattern of pulses over a duration and other parameters may change the intensity as well as the efficacy of the therapy to relieve the symptoms.

As with IMD 110 described above in relation to FIG. 1A, IMD 172 may be constructed of any polymer, metal, or composite material sufficient to house the components of IMD 172 (e.g., components illustrated in FIG. 2) within patient 105. In this example, IMD 172 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 172 may be implanted within other suitable sites within patient 105, which may depend, for example, on the target site within patient 105 for the delivery of electrical stimulation therapy. The outer housing of IMD 172 may be configured to provide a hermetic seal for components, such as a rechargeable or non-rechargeable power source. In addition, in some examples, the outer housing of IMD 172 is selected from a material that facilitates receiving energy to charge the rechargeable power source.

Electrical stimulation energy, which may be constant current or constant voltage pulses, for example, is delivered from IMD 172 to one or more target tissue sites of patient 105 via one or more electrodes 132A and 132B (collectively electrodes 132) of implantable leads 130. In the example of FIG. 1B, leads 130 carry electrodes that are placed adjacent to the target tissue of spinal cord 120. One or more of electrodes 132 may be disposed at a distal tip of a lead 130 and/or at other positions at intermediate points along the lead. Leads 130 may be implanted and coupled to IMD 172. Electrodes 132 may transfer electrical stimulation generated by an electrical stimulation generator in IMD 172 to tissue of patient 105. Electrodes 132 may also sense bioelectrical signals of patient 105.

Although leads 130 may each be a single lead, lead 130 may include a lead extension or other segments that may aid in implantation or positioning of lead 130. In some other examples, IMD 172 may be a leadless stimulator with one or more arrays of electrodes arranged on a housing of the stimulator rather than leads that extend from the housing, as shown in IMD 110 of FIG. 1A. In addition, in some other examples, system 170 may include one lead or more than two leads, each coupled to IMD 172 and directed to similar or different target tissue sites.

Electrodes 132A and 132B of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes 132A and 132B via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 172 through the electrodes of leads 130 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 170 based on one or more factors or user input.

Similarly, sensing bioelectrical signals may use a variety of combinations of electrodes on leads 130, the housing of IMD 172, or other sensors connected directly or indirectly to IMD 172. In some examples, lead 130 includes one or more sensors configured to allow IMD 172 to monitor one or more parameters of patient 105, such as patient activity, pressure, temperature, or other characteristics. The one or more sensors may be provided in addition to, or in place of, therapy delivery by lead 130.

Although FIG. 1B is directed to SCS therapy, e.g., used to treat pain, in other examples system 170 may be configured to treat any other condition that may benefit from electrical stimulation therapy. For example, system 170 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 170 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105. In other examples, IMD 172 takes the form of any combination of deep brain stimulation (DBS) devices, implantable cardioverter defibrillators (ICDs), pacemakers, cardiac resynchronization therapy devices (CRT-Ds), left ventricular assist devices (LVADs), implantable sensors, orthopedic devices, drug pumps and so on.

IMD 172 is configured to deliver electrical stimulation therapy to patient 105 via selected combinations of electrodes carried by one or both of leads 130, alone or in combination with an electrode carried by or defined by an outer housing of IMD 172. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1B, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 172 is configured to generate and deliver electrical stimulation therapy to a target stimulation site within patient 105 via the electrodes of leads 130 to patient 105 according to one or more therapy stimulation programs. A therapy stimulation program defines values for one or more parameters (e.g., a parameter set) that define an aspect of the therapy delivered by IMD 172 according to that program. For example, a therapy stimulation program that controls delivery of stimulation by IMD 172 in the form of pulses may define values for voltage or current pulse amplitude, pulse width, pulse rate (e.g., pulse frequency), electrode combination, pulse shape, etc. for stimulation pulses delivered by IMD 172 according to that program. In some examples, parameters may include sequences of pulses, for example a "burst" of pulses with gradually increasing current magnitudes, or some other sequence. In some examples, IMD 172 may deliver therapy for a given duration and stop delivering therapy for a given duration. In other words, parameters of the electrical stimulation therapy may include an ON-time and an OFF-time. In some examples, an ON-time may be a few seconds or minutes and the OFF-time may also be for a few seconds or minutes. The ON-time may be equal to the OFF-time in some examples, while in other examples the ON-time and the OFF-time may be unequal durations.

Furthermore, IMD 172 may be configured to deliver control stimulation to patient 105 via a combination of electrodes of leads 130, alone or in combination with an electrode carried by or defined by an outer housing of IMD 172 in order to detect ECAP signals (e.g., control pulses and/or informed pulses). The tissue targeted by the stimulation may be the same or similar tissue targeted by the electrical stimulation therapy, but IMD 172 may deliver stimulation pulses for ECAP signal detection via the same, at least some of the same, or different electrodes. Since control stimulation pulses can be delivered in an interleaved manner with informed pulses (e.g., when the pulses configured to contribute to therapy interfere with the detection of ECAP signals or pulse sweeps intended for posture state detection via ECAP signals do not correspond to pulses intended for therapy purposes), a clinician and/or user may select any desired electrode combination for informed pulses. Like the electrical stimulation therapy, the control stimulation may be in the form of electrical stimulation pulses or continuous waveforms.

In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 172 may sense the ECAP signal via two or more electrodes on leads 130. In cases where the control stimulation pulses are applied to spinal cord 120, the signal may be sensed by IMD 172 from spinal cord 120.

In the example of FIG. 1B, external computing device 150 may be placed near IMD 172 to communicate and/or transfer power to IMD 172. In some examples, external computing device 150 may be held in place by a belt or straps 152. In some examples belt 152 may include a pouch that accepts external computing device 150. For implant locations on the hip, as shown in FIG. 1B, patient 105 may find it difficult to position the primary coil of external computing device 150 and to maintain the relative position of the primary and secondary coils. The delivered haptic stimulation of this disclosure may provide feedback to patient 105, based on the quality of alignment of the primary coil and secondary coil, to adjust the position of external computing device 150. In some examples, the haptic stimulation may operate separately from, or in conjunction with a user interface of system 170. Examples of the user interface may include indicator lights, audio feedback, or graphics displayed on a graphical user interface (GUI) such as a tablet computer, smart phone and so on of servers 112.

In some examples, the stimulation generation circuitry of IMD 172 may deliver electrical stimulation therapy to treat a condition of the patient; and interleaved with the electrical stimulation therapy, deliver electrical stimulation to the patient above a perception threshold of the patient. In other words, processing circuitry of system 170 may be configured to deliver electrical stimulation therapy with the appropriate parameter settings to treat pain, tremors, and so on of patient 105. In some examples IMD 172 may briefly pause the delivery of electrical stimulation therapy to deliver haptic stimulation based on the quality of alignment between the primary coil and secondary coil. In other examples, IMD 172 may output haptic stimulation during time frames in which IMD 172 is not delivering electrical stimulation therapy. As described above in relation to FIG. 1A, processing circuitry of system 170 may determine the quality of alignment based on any combination of system metrics. As noted above, some examples of system metrics may include a power reception efficiency, a power transfer efficiency, electrical current magnitude, calculated amount of heat, and so on. In some examples system metrics may include an indication of a metal detection magnitude, e.g., based on the proximity of the primary coil to the housing of IMD 172.

In some examples, a user, such as a clinician or patient 105, may interact with a user interface of an external computing device, such as external computing device 150 or server 112, to program IMD 172. In some examples, external computing device 150 may also be referred to as a programmer. Programming of IMD 172 may refer generally to the generation and transfer of commands, programs, or other information to control the operation of IMD 172. In this manner, IMD 172 may receive the transferred commands and programs from external computing device 150 to control stimulation, such as electrical stimulation therapy (e.g., informed pulses), control stimulation (e.g., control pulses), haptic stimulation, sensing and so on. For example, external computing device 150 may transmit therapy stimulation programs, ECAP test stimulation programs, stimulation parameter adjustments, therapy stimulation program selections, ECAP test program selections, user input, or other information to control the operation of IMD 172, e.g., by wireless telemetry or wired connection.

As described above in relation to FIG.1A, information may be transmitted between external computing device 150 and IMD 172. Therefore, IMD 172 and external computing device 150 may communicate via wireless communication using any techniques known in the art. Examples of communication techniques may include, for example, radiofrequency (RF) telemetry and inductive coupling, but other techniques are also contemplated. In some examples, external computing device 150 includes a communication head, e.g., antenna 26 depicted in FIG. 1A, that may be placed proximate to the patient's body near the IMD 172 implant site to improve the quality or security of communication between IMD 172 and external computing device 150. Communication between external computing device 150 and IMD 172 may occur during power transmission or separate from power transmission.

In the example of FIG. 1B, IMD 172 described as performing a plurality of processing and computing functions. However, external computing device 150 and/or servers 112 instead may perform one, several, or all of these functions. In this alternative example, IMD 172 functions to relay sensed signals to external computing device 150 for analysis, and external computing device 150 transmits instructions to IMD 172 to adjust the one or more parameters defining the electrical stimulation therapy based on analysis of the sensed signals. For example, IMD 172 may relay the sensed signal indicative of an ECAP to external computing device 150. External computing device 150 may compare the parameter value of the ECAP to the target ECAP characteristic value, and in response to the comparison, external computing device 150 may instruct IMD 172 to adjust one or more stimulation parameter that defines the electrical stimulation informed pulses and, in some examples, control pulses, delivered to patient 105.

Figure 2:
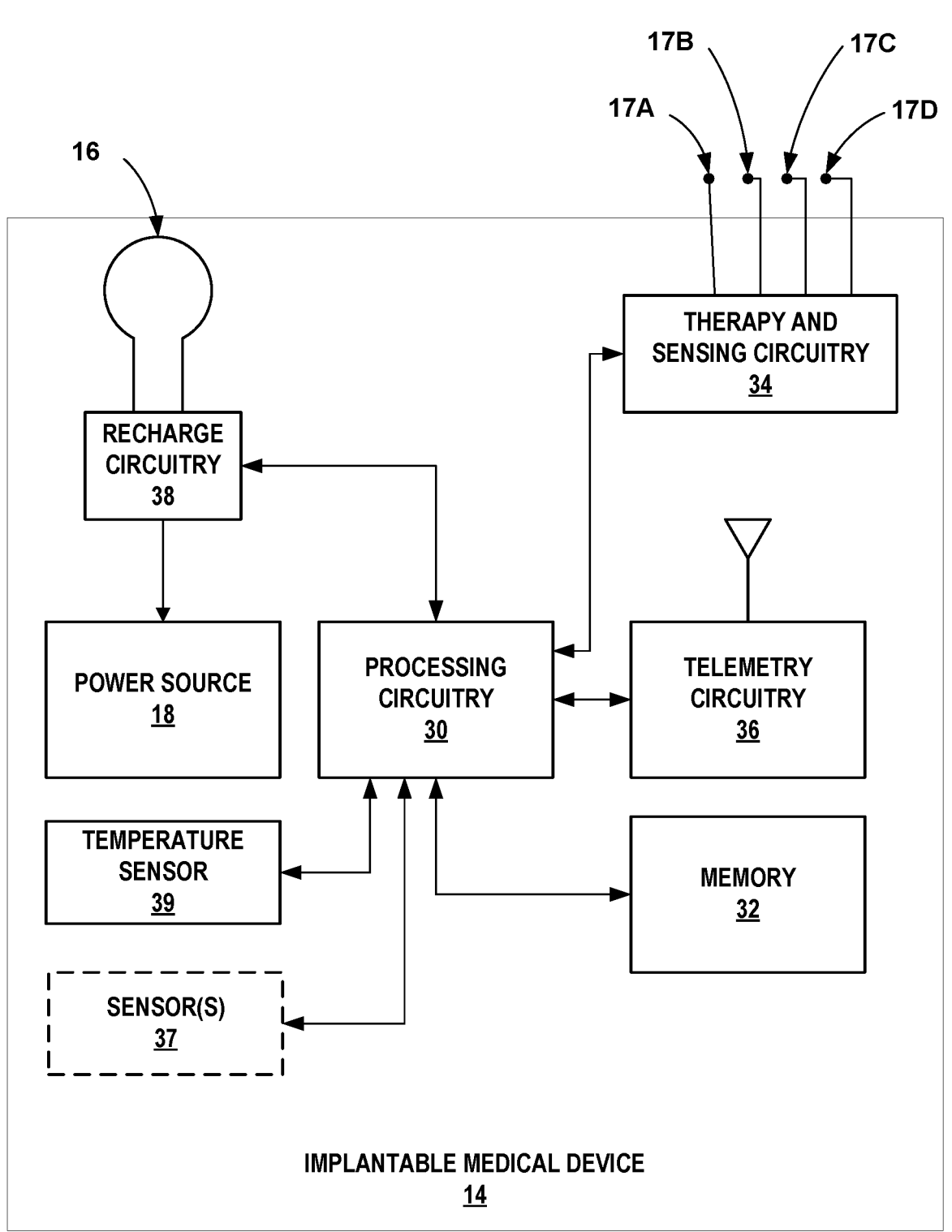
FIG. 2 is a block diagram illustrating example components of the implantable medical device of FIGS. 1A and 1B.

FIG. 2 is a block diagram illustrating example components of the medical device of FIG. 1A. Implantable medical device 14 is an example of device 10 described above in relation to FIG. 1A and IMD 172 of FIG. 2 and may have the same or similar functions and characteristics. In the example illustrated in FIG. 2, IMD 14 includes temperature sensor 39, coil 16, processing circuitry 30, therapy and sensing circuitry 34, recharge circuitry 38, memory 32, telemetry circuitry 36, power source 18, and one or more sensors 37, such as an accelerometer. In other examples, IMD 14 may include a greater or a fewer number of components, e.g., in some examples, IMD 14 may not include temperature sensor 39 or sensors 37. In general, IMD 14 may comprise any suitable arrangement of hardware, alone or in combination with software and/or firmware, to perform the various techniques described herein attributed to IMD 14 and processing circuitry 30, and any equivalents thereof.

Processing circuitry 30 of IMD 14 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the processing circuitry 30 to perform the actions attributed to this circuitry. Moreover, although processing circuitry 30, therapy and sensing circuitry 34, recharge circuitry 38, telemetry circuitry 36, and temperature sensor 39 are described as separate modules, in some examples, some combination of processing circuitry 30, therapy and sensing circuitry 34, recharge circuitry 38, telemetry circuitry 36 and temperature sensor 39 are functionally integrated. In some examples, processing circuitry 30, therapy and sensing circuitry 34, recharge circuitry 38, telemetry circuitry 36, and temperature sensor 39 correspond to individual hardware units, such as ASICs, DSPs, FPGAs, or other hardware units. For example, components of IMD 14 may be implemented as separate circuits in some examples. In other examples, two or more components of IMD 14 may be implemented on a single integrated circuit, e.g., including processing circuitry 30, telemetry circuitry 36, memory 32, therapy and sensing circuitry 34, and so on. In this disclosure, therapy, and sensing circuitry 34 may be referred to as therapy circuitry 34, for simplicity.

Memory 32 may store therapy programs or other instructions that specify therapy parameter values for the therapy provided by therapy circuitry 34 and IMD 14. In some examples, memory 32 may also store temperature data from temperature sensor 39, instructions for recharging rechargeable power source 18, thresholds, instructions for communication between IMD 14 and an external computing device, or any other instructions required to perform tasks attributed to IMD 14. Memory 32 may be configured to store instructions for communication with and/or controlling one or more temperature sensors of temperature sensor 39. In various examples, memory 32 stores information related to determining the temperature of housing 19 and/or exterior surface (s) of housing 19 of IMD 14 based on temperatures sensed by one or more temperature sensors, such as temperature sensor 39, located within IMD 14.

For example, memory 32 may store programming settings such as parameters for electrical stimulation therapy output, e.g., magnitude, pulse width, and so on. Memory 32 may store parameters and other settings for the delivery of haptic stimulation. Settings may be individualized based on patient preference and/or patient physiology. For example, a stimulation intensity that is above the perception threshold for a first patient may be different than the stimulation intensity that may be above the perception threshold for a second patient. In some examples, a patient may find a particular frequency to be annoying or painful and therefore, may prefer a different frequency setting when receiving haptic stimulation as feedback.

Instructions stored at memory 32 when executed by processing circuitry 30 may determine whether a sensed bioelectrical signal is valid, such as and ECAP or other signal in response to an output electrical stimulation therapy event. Memory 32 may store programming instructions that when executed by processing circuitry 30 cause processing circuitry 30 to cause electrical stimulation circuitry therapy circuitry 34 to deliver electrical stimulation therapy to a target nerve of a patient.

Therapy and sensing circuitry 34 may generate and deliver electrical stimulation under the control of processing circuitry 30. Therapy and sensing circuitry 34 may also output non-therapy stimulation, such as control pulses and haptic stimulation. In some examples, processing circuitry 30 controls therapy circuitry 34 by accessing memory 32 to selectively access and load at least one of the stimulation programs to therapy circuitry 34. For example, in operation, processing circuitry 30 may access memory 32 to load one of the stimulation programs to therapy circuitry 34. In such examples, relevant stimulation parameters may include a voltage amplitude, a current amplitude, a pulse rate, a pulse width, a duty cycle, or the combination of electrodes 17A, 17B, 17C, and 17D (collectively "electrodes 17") that therapy circuitry 34 may use to deliver the electrical stimulation signal as well as sense biological signals. In other examples, IMD 14 may have more or fewer electrodes than the four shown in the example of FIG. 2. In some examples electrodes 17 may be part of or attached to a housing of IMD 14, e.g., a leadless electrode. In other examples, one or more of electrodes 17 may be part of a lead implanted in or attached to a patient to sense biological signals and/or deliver electrical stimulation, as described above in relation to FIG. 1A.

In some examples, one or more electrodes connected to therapy circuitry 34 may connect to one or more sensing electrodes, e.g., attached to housing of IMD 14. In some examples the electrodes may be configured to detect an evoked motor response caused by the electrical stimulation therapy event, or other bioelectrical signals such as ECAPs, impedance and so on.

IMD 14 also includes components to receive power to recharge rechargeable power source 18 when rechargeable power source 18 has been at least partially depleted. As shown in FIG. 2, IMD 14 includes coil 16 and recharge circuitry 38 coupled to rechargeable power source 18. Recharge circuitry 38 may be configured to charge rechargeable power source 18 with the selected power level determined by either processing circuitry 30 or an external charging device, such as external computing device 110 described above in relation to FIG. 1A. Recharge circuitry 38 may include any of a variety of charging and/or control circuitry configured to process or convert current induced in coil 16 into charging current to charge power source 18. For example, recharge circuitry 38 may include measurement circuitry configured to determine a magnitude of current received by secondary coil 16, a magnitude of current delivered to power source 18, and other measurements. Recharge circuitry 38 may send such measurements to processing circuitry 30 to be used in system metrics, e.g., to determine a quality of alignment.

Secondary coil 16 may include a coil of wire or other device capable of inductive coupling with a primary coil disposed external to patient 12. Although secondary coil 16 is illustrated as a simple loop of in FIG. 2, secondary coil 16 may include multiple turns of conductive wire. Secondary coil 16 may include a winding of wire configured such that an electrical current can be induced within secondary coil 16 from a magnetic field. The induced electrical current may then be used to recharge rechargeable power source 18.

Recharge circuitry 38 may include one or more circuits that process, filter, convert and/or transform the electrical signal induced in the secondary coil to an electrical signal capable of recharging rechargeable power source 18. For example, in alternating current induction, recharge circuitry 38 may include a half-wave rectifier circuit and/or a full-wave rectifier circuit configured to convert alternating current from the induction to a direct current for rechargeable power source 18. The full-wave rectifier circuit may be more efficient at converting the induced energy for rechargeable power source 18. However, a half-wave rectifier circuit may be used to store energy in rechargeable power source 18 at a slower rate. In some examples, recharge circuitry 38 may include both a full-wave rectifier circuit and a half-wave rectifier circuit such that recharge circuitry 38 may switch between each circuit to control the charging rate of rechargeable power source 18 and temperature of IMD 14.

Rechargeable power source 18 may include one or more capacitors, batteries, and/or other energy storage devices. Rechargeable power source 18 may deliver operating power to the components of IMD 14. In some examples, rechargeable power source 18 may include a power generation circuit to produce the operating power. Rechargeable power source 18 may be configured to operate through many discharge and recharge cycles. Rechargeable power source 18 may also be configured to provide operational power to IMD 14 during the recharge process. In some examples, rechargeable power source 18 may be constructed with materials to reduce the amount of heat generated during charging. In other examples, IMD 14 may be constructed of materials and/or using structures that may help dissipate generated heat at rechargeable power source 18, recharge circuitry 38, and/or secondary coil 16 over a larger surface area of the housing of IMD 14.

Although rechargeable power source 18, recharge circuitry 38, and secondary coil 16 are shown as contained within the housing of IMD 14, in alternative implementations, at least one of these components may be disposed outside of the housing. For example, in some implementations, secondary coil 16 may be disposed outside of the housing of IMD 14 to facilitate better coupling between secondary coil 16 and the primary coil of external charging device. In other examples, power source 18 may be a primary power cell and IMD 14 may not include recharge circuitry 38 and recharge coil 16.

Processing circuitry 30 may also control the exchange of information with an external computing device using telemetry circuitry 36. In the example of FIG. 2, telemetry circuitry 36 may be configured for wireless communication using radio frequency protocols, such as BLUETOOTH, or similar RF protocols, as well as using inductive communication protocols. Telemetry circuitry 36 may include one or more antennas 37 configured to communicate with external charging device, for example. Processing circuitry 30 may transmit operational information and receive therapy programs or therapy parameter adjustments via telemetry circuitry 36. Also, in some examples, IMD 14 may communicate with other implanted devices, such as stimulators, control devices, or sensors, via telemetry circuitry 36. In addition, telemetry circuitry 36 may be configured to control the exchange of information related to sensed and/or determined temperature data, for example temperatures sensed by and/or determined from temperatures sensed using temperature sensor 39. In some examples, telemetry circuitry 36 may communicate using inductive communication, and in other examples, telemetry circuitry 36 may communicate using RF frequencies separate from the frequencies used for inductive charging.

In some examples, processing circuitry 30 may transmit additional information to external charging device related to the operation of rechargeable power source 18. For example, processing circuitry 30 may use telemetry circuitry 36 to transmit indications that rechargeable power source 18 is completely charged, rechargeable power source 18 is fully discharged, the amount of charging current output by recharge circuitry 38 e.g., to power source 18, or any other charge status of rechargeable power source 18. In some examples, processing circuitry 30 may use telemetry circuitry 36 to transmit instructions to external charging device, including instructions regarding further control of the charging session, for example instructions to lower the power level or to terminate the charging session, based on the determined temperature of the housing/external surface 19 of the IMD.

Processing circuitry 30 may also transmit information to external charging device that indicates any problems or errors with rechargeable power source 18 that may prevent rechargeable power source 18 from providing operational power to the components of IMD 14. In various examples, processing circuitry 30 may receive, through telemetry circuitry 36, instructions for algorithms, including formulas and/or values for constants to be used in the formulas, which may be used to determine the temperature of the housing 19 and/or exterior surface(s) of housing 19 of IMD 14 based on temperatures sensed by temperature sensor 39 located within IMD 14 during and after a recharging session performed on rechargeable power source 18.

Figure 3:
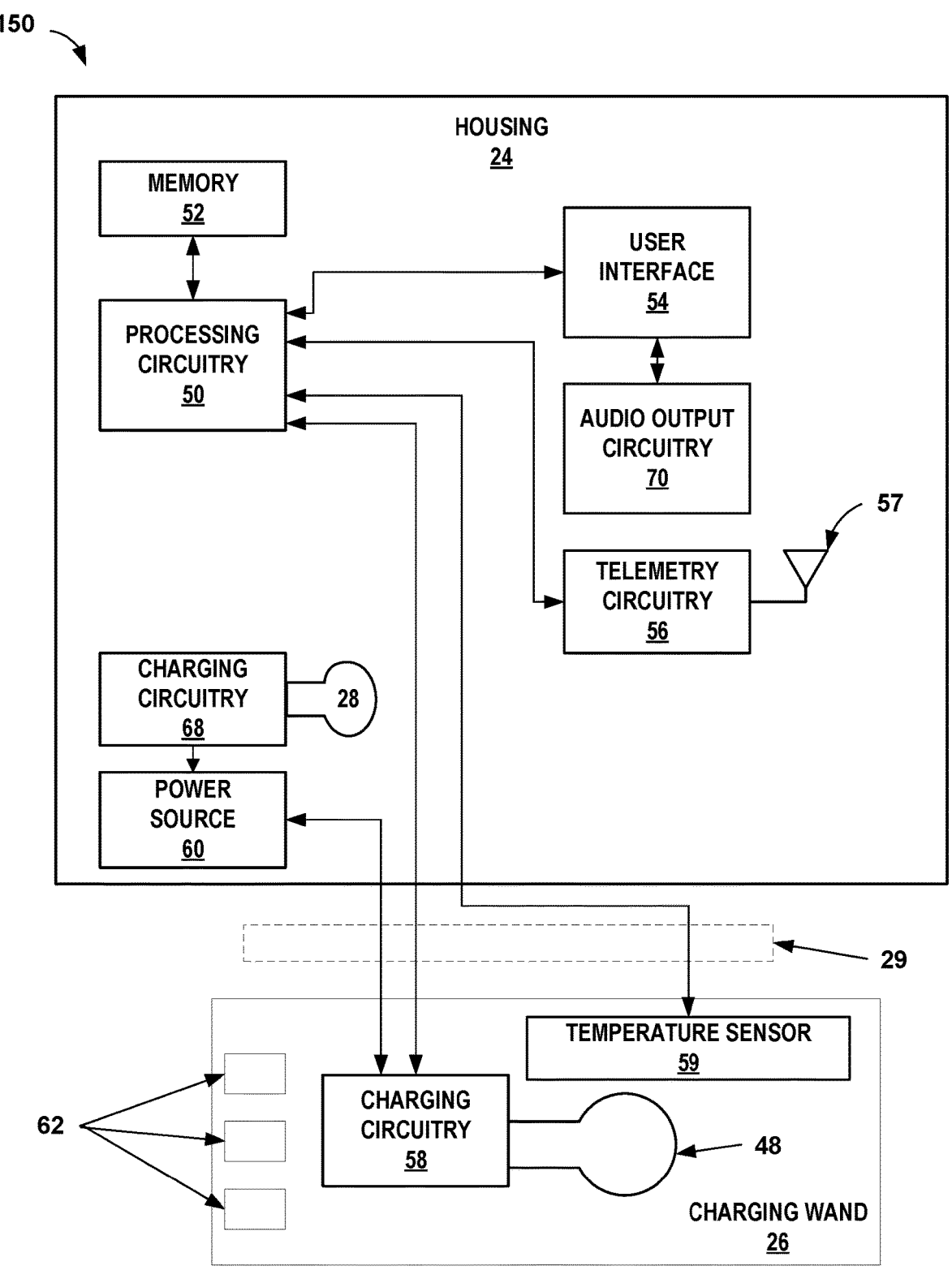
FIG. 3 is a block diagram of an example external charging device of FIGS. 1A and 1B.

FIG. 3 is a block diagram of an example an external computing device of FIGS. 1A and 1B. External charging device 150 in of FIG. 2 is an example of external computing device 150 described above in relation to FIGS. 1A and 1B. As described above, in some examples, external charging device 150 may be a hand-held device, in other examples, external charging device 150 may be a larger or a non-portable device. In addition, in other examples external charging device 150 may be included as part of an external programmer or include functionality of an external programmer. As shown in the example of FIG. 3, external charging device 150 includes two separate components. Housing 24 encloses components such as a processing circuitry 50, memory 52, user interface 54, telemetry circuitry 56, power button, audio output circuitry 70 and power source 60. Charging head 26, also referred to as a charging wand 26, may include charging circuitry 58, temperature sensor 59, and coil 48. Housing 24 is electrically coupled to charging head 26 via charging cable 29. In some examples, housing 24 may also include charging circuitry 68 and coil 28, which is an example of coil 28 described above in relation to FIGS. 1A and 1B.

In some examples, separate charging wand 26 may facilitate positioning of coil 48 over coil 16 of IMD 14. In some examples, charging circuitry 68 and/or coil 28 may be integrated within housing 24 in other examples, as described above in relation to FIGS. 1A, 1B. In other examples, external charging device 150 may not include charging wand 26. Memory 52 may store instructions that, when executed by processing circuitry 50, causes processing circuitry 50 and external charging device 150 to provide the functionality ascribed to external charging device 150 throughout this disclosure, and/or any equivalents thereof. Coil 48 and coil 28 may also be referred to as an antenna.

External charging device 150 may also include one or more temperature sensors, illustrated as temperature sensor 59, similar to temperature sensor 39 of FIG. 2. As shown in FIG. 3, temperature sensor 59 may be disposed within charging head 26. For example, charging head 26 may include one or more temperature sensors positioned and configured to sense the temperature of coil 48 and/or a surface of the housing of charging head 26. In some examples, external charging device 150 may not include temperature sensor 59. In other examples, one or more temperature sensors of temperature sensor 59 may be disposed within housing 24, such as located to sense the temperature of primary coil 28 and/or charging circuitry 68.

In general, external charging device 150 comprises any suitable arrangement of hardware, alone or in combination with software and/or firmware, to perform the techniques ascribed to external charging device 150, and processing circuitry 50, user interface 54, telemetry circuitry 56, and charging circuitry 58 of external charging device 150, and/or any equivalents thereof. In various examples, external charging device 150 may include one or more processors, such as one or more microprocessors, DSPs, ASICs, FPGAs, or any other equivalent integrated or discrete logic circuitry, as well as any combinations of such components Similar to IMD 14, components of external charging device 150 shown in FIG. 3 may be implemented as separate circuitry, or combined into one or more integrated circuits.

In other words, although processing circuitry 50, telemetry circuitry 56, charging circuitry 58, and temperature sensor 59 are described as separate modules, in some examples, processing circuitry 50, telemetry circuitry 56, charging circuitry 58, and/or temperature sensor 59 are functionally integrated. In some examples, processing circuitry 50, telemetry circuitry 56, charging circuitry 58, and/or temperature sensor 59 correspond to individual hardware units, such as ASICs, DSPs, FPGAs, or other hardware units. External charging device 150 also, in various examples, may include a memory 52, such as RAM, ROM, PROM, EPROM, EEPROM, flash memory, a hard disk, a CD-ROM, comprising executable instructions for causing the one or more processors to perform the actions attributed to them.

Memory 52 may store instructions that, when executed by processing circuitry 50, cause processing circuitry 50 and external charging device 150 to provide the functionality ascribed to external charging device 150 throughout this disclosure, and/or any equivalents thereof. For example, memory 52 may include instructions that cause processing circuitry 50 to control the power level used to charge IMD 14 in response to the determined temperatures for the housing/external surface(s) of IMD 14, as communicated from IMD 14, or instructions for any other functionality. Memory 52 may include a record of selected power levels, sensed temperatures, determined temperatures, or any other data related to charging rechargeable power source 18, described above in relation to FIG. 2.

Processing circuitry 50 may, when requested, transmit any stored data in memory 52 to another computing device for review or further processing, such as to servers 112 depicted in FIGS. 1A, 1B. Processing circuitry 50 may be configured to access memory, such as memory 32 of IMD 14 and/or memory 52 of external charging device 150, to retrieve information comprising instructions, formulas, and determined values for one or more constants.

User interface 54 may include buttons, a keypad, indicator lights, a microphone for voice commands, a display, such as a liquid crystal (LCD), light-emitting diode (LED), or cathode ray tube (CRT) and audio output circuitry 70. In some examples, user interface 54 may include a component to output vibration, such as a vibration motor, or may use audio output circuitry 70 to output vibration for haptic feedback. In some examples, user interface 54 may also connect to one or more skin electrodes 62, which may be configured to provide stimulation for haptic feedback when at least two electrodes are in contact with the skin of the patient.

In some examples, the display of user interface 54 may be a touch screen. As discussed in this disclosure, processing circuitry 50 may present and receive information relating to the charging of rechargeable power source 18 via user interface 54. For example, user interface 54 may indicate when charging is occurring, quality of the alignment between primary coil 28 or 48 and the secondary coil of the IMD, the selected power level, current charge level of rechargeable power source 18, duration of the current recharge session, anticipated remaining time of the charging session, sensed temperatures, or any other information. In some examples, processing circuitry 50 may receive some of the information displayed on user interface 54 from IMD 14, e.g., via communication circuitry such as telemetry circuitry 56. In some examples, user interface 54 may provide an indication to the user regarding the quality of alignment between coil 16, depicted in FIG. 2 and coil 48, based on one or more system metrics, such as the charge current to the battery of the IMD.

Processing circuitry 50 may also receive user input via user interface 54. The input may be, for example, in the form of pressing a button on a keypad or selecting an icon from a touch screen. The input may change programmed settings, start, or stop therapy, request starting or stopping a recharge session, a desired level of charging, or one or more statistics related to charging rechargeable power source 18 (e.g., the cumulative thermal dose). In this manner, user interface 54 may allow the user to view information related to the operation of IMD 14.

Charging circuitry 58 may include one or more circuits that generate an electrical signal, and an electrical current, within primary coil 48. Charging circuitry 58 may generate an alternating current of specified amplitude and frequency in some examples. In other examples, charging circuitry 58 may generate a direct current. In any case, charging circuitry 58 may be capable of generating electrical signals, and subsequent magnetic fields, to transmit various levels of power to IMD 14. In this manner, charging circuitry 58 may be configured to charge rechargeable power source 18 of IMD 14 with the selected power level.

Power source 60 may deliver operating power to the components of external charging device 150. Power source 60 may also deliver the operating power to drive primary coil 48 or primary coil 28 during the charging process. Power source 60 may include a battery and a power generation circuit to produce the operating power. In some examples, a battery of power source 60 may be rechargeable to allow extended portable operation. In other examples, power source 60 may draw power from a wired voltage source such as a consumer or commercial power outlet.

Telemetry circuitry 56 supports wireless communication between IMD 14 and external charging device 150 under the control of processing circuitry 50. Telemetry circuitry 56 may also be configured to communicate with another computing device via wireless communication techniques, or direct communication through a wired connection. In some examples, telemetry circuitry 56 may be substantially similar to telemetry circuitry 36 of IMD 14 described herein, providing wireless communication via an RF or proximal inductive medium. In some examples, telemetry circuitry 56 may include an antenna 57, which may take on a variety of forms, such as an internal or external antenna. Although telemetry circuitry 56 and 36 may each include dedicated antennas for communications between these devices, telemetry circuitry 56 and 36 may instead, or additionally, be configured to utilize inductive coupling from coils 16 and 48 to transfer data.

Examples of local wireless communication techniques that may be employed to facilitate communication between external charging device 150 and IMD 14 include radio frequency and/or inductive communication according to any of a variety of standard or proprietary telemetry protocols, or according to other telemetry protocols such as the IEEE 802.11x or Bluetooth specification sets. In this manner, other external devices may be capable of communicating with external charging device 150 without needing to establish a secure wireless connection.

In operation, processing circuitry 50, and or secondary processing circuitry 40, may control user interface 54 to provide information to a user about communication status, charging efficiency, therapy status of the IMD and so on. For example, processing circuitry 50 may determine whether communication circuitry, e.g., telemetry circuitry 56, has established a communication link with the power receiving device, device 10 and IMD 110 depicted in FIGS. 1A, 1B, and 2.

As described above in relation to FIGS. 1A, 1B, and 2, processing circuitry 50 may use any one or more system metrics to determine power transfer to device 10. In some examples, device 10 may send a signal indicating an amount of current output by the recharge circuitry of device 10. In other examples, processing circuitry 50 may calculate other system metrics, such as alignment of coil 28 to coil 16 of device 10 using any of several techniques, including heat calculations, temperature measurements, detection of metal, and so on. Processing circuitry may compare any of the calculated power transfer, power efficiency, alignment, IMD current, etc. to a threshold stored at memory 52. In some examples, based on the comparison, processing circuitry 30 may transmit commands or information to the IMD to control haptic stimulation delivered by the IMD.

Memory 52 may store several power coupling thresholds. A calculated power transfer metric (e.g., efficiency, magnitude of current, etc.) below a first threshold may indicate poor coupling. A power transfer metric above the first threshold but less than a second threshold may indicate "good" coupling. A power transfer metric above the second threshold but less than a third threshold may indicate "excellent" coupling, and so on. In some examples, responsive to determining that the power receiving device is receiving wireless power above the first threshold and receiving wireless power below the second threshold, processing circuitry 50 may control user interface 54 to display an indication of the quality of alignment, based on the magnitude of received wireless power. As described above in relation to FIGS. 1A-2, processing circuitry 50 may transmit information to the IMD to control delivered haptic stimulation based on the indication of the quality of alignment.

In some examples, processing circuitry 50 may also output an audio tone, pattern, and so on via audio output circuitry 70. In some examples, the audio pattern may be selectable by a user, such as the patient, based on the type of information that processing circuitry 50 is programmed to output. Some examples of patterns may include a warble tone, a distinctive musical sequence (e.g., shave and a haircut, Smoke on the Water intro, etc.) and so on. For example, responsive to determining that the power receiving device is receiving wireless power above the first threshold and receiving wireless power below a second threshold, processing circuitry 50 may cause audio circuitry to output an audible alert with a first audible pattern. Processing circuitry 50 may cause audio output circuitry 70 to output other audio tones, patterns and so on for any of the conditions or states described herein, e.g., therapy on or off, and so on.

FIG. 4 is a flowchart illustrating an example operation of the medical system 100 of this disclosure. The example of FIG. 4 is described with respect to system 100 of FIG. 1A. However, the same techniques may be applied to system 170 of FIG. 1B or any other described devices and systems. As described above in relation to FIGS. 1A, a power transmitting device, such as external computing device 150 may transmit wireless electrical energy via a power transmitting antenna, e.g., primary coil 26 or primary coil 28 (90). Next, a power receiving device, such as implantable medical devices 10 and 172 may receive at least a portion of the wireless electrical energy from the power transmitting device (92). As described above in relation to FIG. 2, IMD 14 may include power receiving circuitry, e.g., recharge circuitry 38 and secondary coil 16.

Next, processing circuitry of system 100, or 170 depicted in FIGS. 1A and 1B respectively, may determine an indication of a quality of alignment between the power transmitting antenna, primary coil 26 or 28 and the IMD (94). As described above in relation to FIGS. 1A and 1B the alignment between the primary coil and components of the IMD, such as secondary coil 16, the housing, the header and so on, may impact one or more system metrics. In some examples, alignment with the header of the IMD may cause heating of the IMD, but different alignment positions may affect the ratio of power transmitted compared to power received by the IMD battery.

Responsive to determining the quality of alignment, processing circuitry of the system may control stimulation circuitry of the IMD to deliver haptic stimulation representative of the quality of alignment to a patient (96). As described above in relation to FIGS. 1A-3, processing circuitry of any of servers 112, IMD 10 and/or external computing device 150 may execute programming instructions to determine of the quality of alignment and the haptic stimulation parameter settings.

The techniques of this disclosure may also be described in the following examples.

Example 1: An implantable medical device comprising a memory; power receiving circuitry configured to receive wireless electrical energy; stimulation generation circuitry configured to deliver electrical stimulation therapy to the patient via a plurality of electrodes; and processing circuitry operably coupled to the memory, the processing circuitry configured to: control the stimulation generation circuitry to deliver the electrical stimulation therapy to a patient; receive an indication of a quality of alignment with a power transmitting device; and responsive to the indication of the quality of alignment, cause the stimulation generation circuitry to deliver haptic stimulation representative of the quality of alignment.

Example 2: The device of example 1, wherein the processing circuitry is configured to cause the stimulation generation circuitry to deliver the haptic stimulation by at least causing the stimulation generation circuitry to adjust haptic electrical stimulation to the patient above a perception threshold of the patient, the haptic electrical stimulation being different than the electrical stimulation therapy.

Example 3: The device of any of examples 1 and 2, wherein the processing circuitry is configured to cause the stimulation generation circuitry to deliver the haptic stimulation by at least increasing a stimulation intensity of the electrical stimulation therapy higher than a perception threshold of the patient.

Example 4: The device of any of examples 1 through 3, wherein to deliver haptic stimulation the processing circuitry is configured to control the stimulation generation circuitry to: deliver electrical stimulation therapy to treat a condition of the patient; and interleaved with the electrical stimulation therapy, deliver electrical stimulation to the patient above a perception threshold of the patient.

Example 5: The device of any of examples 1 through 4, wherein the indication of the quality of alignment is based on a determination that the device is receiving power relative to a power threshold.

Example 6: The device of example 5, wherein the processing circuitry is configured to: responsive to determining that the device is receiving wireless power above a first threshold and receiving wireless power below a second threshold, cause the electrical stimulation circuitry to deliver the haptic stimulation at a first frequency, and responsive to determining that the device is receiving wireless power above the first threshold and above the second threshold cause the electrical stimulation circuitry to deliver the haptic stimulation at a second frequency.

Example 7: The device of any of examples 1 through 6, wherein the processing circuitry is further configured to, responsive to determining that the quality of alignment is above a threshold, cause the electrical stimulation circuitry to indicate the quality of alignment by adjusting the delivered haptic stimulation to reduce a stimulation intensity of the delivered haptic stimulation to below than a perception threshold of the patient.

Example 8: The device of any of examples 1 through 7, wherein an intensity of the haptic stimulation is inversely proportional to the quality of alignment; and wherein as the quality of alignment decreases, the intensity of the haptic stimulation increases above a perception threshold of the patient.

Example 9: The device of any of examples 1 through 8, wherein the indication of the quality of alignment is based on the processing circuitry of the device receiving an indication of power transfer efficiency.

Example 10: The device of any of examples 1 through 9, wherein the indication of the quality of alignment is based on the processing circuitry of the device determining a power reception efficiency.

Example 11: The device of any of examples 1 through 10, wherein the indication of the quality of alignment is based on the processing circuitry of the device receiving an indication of a metal detection magnitude.

Example 12: The device of any of examples 1 through 11, wherein the indication of the quality of alignment is based on the processing circuitry of the device receiving an indication of an estimate for an amount of heating of the device.

Example 13: The device of any of examples 1 through 12, further comprising receive information indicative of the ECAP signal elicited by the haptic stimulation; and deliver, based on the ECAP signal, the haptic stimulation at an intensity level above a perception threshold of the patient.

Example 14: A method comprising transmitting, by a power transmitting device, wireless electrical energy via a power transmitting antenna; receiving, by power receiving circuitry of an implantable medical device (IMD), at least a portion of the wireless electrical energy from the power transmitting device; determining a quality of alignment between the power transmitting antenna and the IMD; and responsive to determining the quality of alignment, delivering, by the IMD, haptic stimulation representative of the quality of alignment to a patient.

Example 15: The method of example 14, wherein delivering the haptic stimulation comprises controlling, by processing circuitry of the IMD, stimulation generation circuitry of the IMD, and wherein delivering the haptic stimulation comprises increasing a stimulation intensity of electrical stimulation higher than a perception threshold of the patient.

Example 16: The method of any of examples 14 and 15, wherein delivering haptic stimulation comprises processing circuitry of the IMD causing the stimulation generation circuitry to: deliver electrical stimulation therapy to treat a condition of the patient; and interleaved with the electrical stimulation therapy, deliver electrical stimulation to the patient above a perception threshold of the patient.

Example 17: The method of any of examples 13 through 16, wherein the indication of the quality of alignment is based on a determination that the IMD is receiving power relative to a power threshold.

Example 18: The method of example 17, further comprising responsive to determining that the IMD is receiving wireless power above a first threshold and receiving wireless power below a second threshold, causing the electrical stimulation circuitry to deliver the haptic stimulation at a first frequency, and responsive to determining that the IMD is receiving wireless power above the first threshold and above the second threshold causing the electrical stimulation circuitry to deliver the haptic stimulation at a second frequency.

Example 19: The method of any of examples 17 and 18, further comprising, responsive to determining that the quality of alignment is above a threshold, controlling the electrical stimulation circuitry to indicate the quality of alignment by adjusting the delivered haptic stimulation to reduce a stimulation intensity of the delivered haptic stimulation to below a perception threshold of the patient.

Example 20: The method of any of examples 14 through 19, wherein an intensity of the haptic stimulation is inversely proportional to the quality of alignment; and wherein as the quality of alignment decreases, the intensity of the haptic stimulation increases above a perception threshold of the patient.

Example 21: The method of any of examples 14 through 20, wherein processing circuitry of the IMD determines the quality of alignment, and wherein the processing circuitry of the IMD determines the quality of alignment based on receiving, by the processing circuitry, an indication of the quality of alignment.

Example 22: The method of example 21, wherein the indication of the quality of alignment is based on the processing circuitry of the IMD receiving an indication of power transfer efficiency.

Example 23: The method of any of examples 21 and 22, wherein the indication of the quality of alignment is based on the processing circuitry of the IMD determining a power reception efficiency.

Example 24: The method of any of examples 21 through 23, wherein the indication of the quality of alignment is based on the processing circuitry of the IMD receiving an indication of a metal detection magnitude.

Example 25: The method of any of examples 21 through 24, wherein the indication of the quality of alignment is based on the processing circuitry of the IMD receiving an indication of an estimate for an amount of heating of the IMD.

Example 26: The method of any of examples 21 through 25, further comprising sensing, by sensing circuitry of the IMD, an evoked compound action potential (ECAP) signal elicited by the haptic stimulation, receiving, by the processing circuitry, information indicative of the ECAP signal elicited by the haptic stimulation; and delivering, based on the ECAP signal, the haptic stimulation at an intensity level above a perception threshold of the patient.

Example 27: A system comprising a power transmitting device configured to wirelessly transfer electrical energy, the power transmitting device comprising power transmission circuitry configured to wirelessly output the electrical energy via the power transmitting antenna; and first processing circuitry, the processing circuitry configured to control the power transmission circuitry; and an implantable medical device (IMD) comprising power receiving circuitry, configured to receive at least a portion of wireless electrical energy from the power transmitting device; stimulation generation circuitry configured to deliver electrical stimulation therapy to a patient via a plurality of electrodes; and second processing circuitry, the second processing circuitry configured to: control the stimulation generation circuitry; receive an indication of a quality of alignment with the power transmitting antenna; and responsive to receiving the indication of the quality of alignment, cause the stimulation generation circuitry to deliver haptic stimulation representative of the quality of alignment.

Example 28: The system of example 27, wherein the second processing circuitry is configured to control the stimulation generation circuitry to deliver haptic stimulation by at least adjust a haptic stimulation intensity above a perception threshold of the patient.

Example 29: The system of any of examples 27 and 28, wherein the indication of the quality of alignment received by the second processing circuitry comprises instructions for a specified adjustment to the electrical stimulation therapy transmitted; and wherein responsive to receiving the indication of the quality of alignment including the instructions for the specified adjustment, the second processing circuitry is configured to cause the stimulation generation circuitry to adjust the electrical stimulation based on the specified instructions.

Example 30: The system of example 29, wherein the first processing circuitry is configured to determine the quality of alignment and generate the specified instructions to the electrical stimulation therapy.

Example 31: The system of any of examples 27 through 30, wherein the second processing circuitry is configured to determine the adjustment to the electrical stimulation therapy based on the indication of the quality of alignment.

Example 32: The system of any of examples 27 through 31, wherein the indication of the quality of alignment is based on power transfer efficiency, and wherein the first processing circuitry is further configured to determine the power transfer efficiency.

Example 33: The system of any of examples 27 through 32, wherein the indication of the quality of alignment is based on the second processing circuitry of the IMD determining a power reception efficiency.

Example 34: The system of any of examples 27 through 33, wherein the indication of the quality of alignment is based on an indication of a magnitude of battery current, wherein the first processing circuitry is configured to receive the indication of battery current from the IMD.

Example 34: The system of any of examples 27 through 34, wherein the power transmitting device comprises one or more skin electrodes, wherein the first processing circuitry is configured output electrical stimulation via the one or more skin electrodes based on the quality of alignment; wherein the electrical stimulation via the one or more skin electrodes provides haptic feedback to the patient representative of the quality of alignment.

In one or more examples, the functions described above may be implemented in hardware, software, firmware, or any combination thereof. For example, the various components of FIGS. 2 and 3, such as processing circuitry 30, therapy and sensing circuitry 34, telemetry circuitry 36, processing circuitry 50 and so on may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

The term "non-transitory" may indicate that the storage medium is not embodied in a carrier wave or a propagated signal. In certain examples, a non-transitory storage medium may store data that can, over time, change (e.g., in RAM or cache). By way of example, and not limitation, such computer-readable storage media, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmit-ted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor," and processing circuitry as used herein may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples of the disclosure have been described. These and other examples are within the scope of the following claims.

What is claimed is:

1. An implantable medical device, the device comprising:
   a memory;
   power receiving circuitry configured to receive wireless electrical energy;
   stimulation generation circuitry configured to deliver electrical stimulation therapy to the patient via a plurality of electrodes; and
   processing circuitry operably coupled to the memory, the processing circuitry configured to:
   control the stimulation generation circuitry to deliver the electrical stimulation therapy to a patient;
   receive an indication of a quality of alignment with a power transmitting device; and
   responsive to the indication of the quality of alignment, cause the stimulation generation circuitry to deliver haptic stimulation representative of the quality of alignment.

2. The device of claim 1, wherein the processing circuitry is configured to cause the stimulation generation circuitry to deliver the haptic stimulation by at least causing the stimulation generation circuitry to adjust haptic electrical stimulation to the patient above a perception threshold of the patient, the haptic electrical stimulation being different than the electrical stimulation therapy.

3. The device of claim 1, wherein the processing circuitry is configured to cause the stimulation generation circuitry to deliver the haptic stimulation by at least increasing a stimulation intensity of the electrical stimulation therapy higher than a perception threshold of the patient.

4. The device of claim 1, wherein to deliver haptic stimulation the processing circuitry is configured to control the stimulation generation circuitry to:

deliver electrical stimulation therapy to treat a condition of the patient; and interleaved with the electrical stimulation therapy, deliver electrical stimulation to the patient above a perception threshold of the patient.

5. The device of claim 1, wherein the indication of the quality of alignment is based on a determination that the device is receiving power relative to a power threshold.

6. The device of claim 5, wherein the processing circuitry is configured to:

responsive to determining that the device is receiving wireless power above a first threshold and receiving wireless power below a second threshold, cause the electrical stimulation circuitry to deliver the haptic stimulation at a first frequency, and responsive to determining that the device is receiving wireless power above the first threshold and above the second threshold cause the electrical stimulation circuitry to deliver the haptic stimulation at a second frequency.

7. The device of claim 1, wherein the processing circuitry is further configured to, responsive to determining that the quality of alignment is above a threshold, cause the electrical stimulation circuitry to indicate the quality of alignment by adjusting the delivered haptic stimulation to reduce a stimulation intensity of the delivered haptic stimulation to below than a perception threshold of the patient.

8. The device of claim 1, wherein an intensity of the haptic stimulation is inversely proportional to the quality of alignment; and wherein as the quality of alignment decreases, the intensity of the haptic stimulation increases above a perception threshold of the patient.

9. The device of claim 1, wherein the indication of the quality of alignment is based on the processing circuitry of the device receiving an indication of power transfer efficiency.

10. The device of claim 1, wherein the indication of the quality of alignment is based on the processing circuitry of the device determining a power reception efficiency.

11. The device of claim 1, wherein the indication of the quality of alignment is based on the processing circuitry of the device receiving an indication of an estimate for an amount of heating of the device.

12. The device of claim 1, further comprising sensing circuitry configured to sense an evoked compound action potential (ECAP) signal elicited by the haptic stimulation, wherein the processing circuitry is configured to:

receive information indicative of the ECAP signal elicited by the haptic stimulation; and deliver, based on the ECAP signal, the haptic stimulation at an intensity level above a perception threshold of the patient.

13. A method comprising:

transmitting, by a power transmitting device, wireless electrical energy via a power transmitting antenna;

receiving, by power receiving circuitry of an implantable medical device (IMD), at least a portion of the wireless electrical energy from the power transmitting device;

determining a quality of alignment between the power transmitting antenna and the IMD; and responsive to determining the quality of alignment, delivering, by the IMD, haptic stimulation representative of the quality of alignment to a patient.

14. The method of claim 13, wherein delivering haptic stimulation comprises processing circuitry of the IMD causing the stimulation generation circuitry to:

deliver electrical stimulation therapy to treat a condition of the patient; and interleaved with the electrical stimulation therapy, deliver electrical stimulation to the patient above a perception threshold of the patient.

15. A system comprising:

a power transmitting device configured to wirelessly transfer electrical energy, the power transmitting device comprising:

power transmission circuitry configured to wirelessly output the electrical energy via the power transmitting antenna; and first processing circuitry, the processing circuitry configured to control the power transmission circuitry; and an implantable medical device (IMD) the IMD comprising:

power receiving circuitry, configured to receive at least a portion of wireless electrical energy from the power transmitting device;

stimulation generation circuitry configured to deliver electrical stimulation therapy to a patient via a plurality of electrodes; and second processing circuitry, the second processing circuitry configured to:

control the stimulation generation circuitry;

receive an indication of a quality of alignment with the power transmitting antenna; and responsive to receiving the indication of the quality of alignment, cause the stimulation generation circuitry to deliver haptic stimulation representative of the quality of alignment.

16. The system of claim 15, wherein the second processing circuitry is configured to control the stimulation generation circuitry to deliver haptic stimulation by at least adjust a haptic stimulation intensity above a perception threshold of the patient.

17. The system of claim 15, wherein the indication of the quality of alignment received by the second processing circuitry comprises instructions for a specified adjustment to the electrical stimulation therapy transmitted; and wherein responsive to receiving the indication of the quality of alignment including the instructions for the specified adjustment, the second processing circuitry is configured to cause the stimulation generation circuitry to adjust the electrical stimulation based on the specified instructions.

18. The system of claim 17, wherein the first processing circuitry is configured to determine the quality of alignment and generate the specified instructions to the electrical stimulation therapy.

19. The system of claim 15, wherein the indication of the quality of alignment is based on an indication of a magnitude of battery current, wherein the first processing circuitry is configured to receive the indication of battery current from the IMD.

20. The system of claim 15, wherein the power transmitting device comprises one or more skin electrodes, wherein the first processing circuitry is configured output electrical stimulation via the one or more skin electrodes based on the quality of alignment;

wherein the electrical stimulation via the one or more skin electrodes provides haptic feedback to the patient representative of the quality of alignment.

\* \* \* \* \*